United States Patent
DeVincenzo

(10) Patent No.: US 6,193,509 B1
(45) Date of Patent: *Feb. 27, 2001

(54) BONY ANCHOR EXTENDER

(76) Inventor: John DeVincenzo, 1312 Garden St., San Luis Obispo, CA (US) 93401

( * ) Notice: Subject to any disclaimer, the term of this patent is extended or adjusted under 35 U.S.C. 154(b) by 0 days.

This patent is subject to a terminal disclaimer.

(21) Appl. No.: 09/245,162

(22) Filed: Feb. 4, 1999

Related U.S. Application Data

(63) Continuation-in-part of application No. 09/054,208, filed on Apr. 2, 1998, now Pat. No. 5,938,437.

(51) Int. Cl.⁷ ....................................................... A61C 3/00
(52) U.S. Cl. ................................ 433/18; 433/22; 433/173
(58) Field of Search ................................ 433/17, 18, 20, 433/21, 22, 173

(56) References Cited

U.S. PATENT DOCUMENTS

| | | | |
|---|---|---|---|
| 2,705,367 | * 4/1955 | Berke | 433/20 |
| 3,593,421 | * 7/1971 | Brader | 433/22 |
| 3,683,502 | * 8/1972 | Wallshein | 433/22 |
| 5,071,345 | * 12/1991 | Rosen | 433/173 |
| 5,306,142 | * 4/1994 | Richards | 433/22 |
| 5,505,616 | * 4/1996 | Harwell | 433/21 |
| 5,697,779 | * 12/1997 | Sachdeva et al. | 433/2 |
| 5,836,768 | * 11/1998 | Huskens et al. | 433/24 |

* cited by examiner

Primary Examiner—John J. Wilson
(74) Attorney, Agent, or Firm—Rodgers & Rodgers

(57) ABSTRACT

That portion of any bony anchor which protrudes from the bone can have placed on it a head to which a connector assembly is attached. The free end of this connector assembly attaches to a bar and rigidly holds the bar in place. On the bar, a variety of attachments are placed thereby extending the influence of the bony anchor to other, more ideal locations from which to apply forces to move teeth in all directions.

11 Claims, 4 Drawing Sheets

BONY ANCHOR EXTENDER

This is a continuation-in-part or application Ser. No. 09/054,208 filed Apr. 2. 1998 now Pat. No. 5,938,437.

BACKGROUND OF THE INVENTION

1. Field of the Invention

This invention relates generally to orthodontic treatment techniques and appliances and is particularly concerned with a device which can be attached to a fixed subperiosteal or intrabony anchor and from which forces can be generated to move teeth and correct malocclusions.

2. Discussion of the Prior Art

The use of fixed, immovable bony anchors as rigid objects from which to exert forces to move teeth has been considered in orthodontics for more than twenty years. See, for example, Sherman, A. J., "Bone reaction to orthodontic forces on vitreous carbon dental implants," *American Journal of Orthodontics*, vol. 74, p. 79, 1978, and Smith, J. R., "Bone dynamics associated with the controlled loading of bioglass-coated aluminum oxide endosteal implants," *American Journal of Orthodontics*, vol. 76, p. 618, 1979. These early studies used animal models. and it was not until 1983 that their use was demonstrated in clinical orthodontics. See Creekmore, T. A. and Eklund, M. K., "The possibility of skeletal anchorage," *Journal of Clinical Orthodontics*, vol. 17, p. 266, 1983. Thereafter additional reports of the use of a bony anchor from which to exert forces to move teeth have appeared See, for example, Turley, P. K., Gray, D. W., Kean, L. J. and Roberts, E. W., "Titanium endosseous and vitallium subteriosteal implants as orthodontic anchors for tooth movement in dogs," *Journal of Dental Research*, vol. 63A, p. 334, 1984, and Goodacre, C. J., "Rigid implant anchorage to close a mandibular first molar extraction site, *Journal of Clinical Orthodontics*, vol. 18, p. 693, 1994. More recently, interest has shifted to subperiosteal anchors as described by Block and Hoffman in U.S. Pat. Nos. 5,066,224 and 5,538,427, the article "A new device for absolute anchorage for orthodontics," *Journal of Orthodontics and Dentofacial Orthopedics*, vol. 107, p. 251, 1995 and in application of Devincenzo, application Ser. No. 08/948,731, filed Oct. 20, 1997. See also Kanomi, R., "Mini-implant for Orthodontic Anchorage," *Journal of Clinical Orthodontics*, vol. 31, pp. 763–767, 1997 and Sachdeva, et al U.S. Pat. No. 5,697,779.

All of the above mentioned anchor systems utilize either endosseous or subperiosteal placement and afford rigid, immovable objects from which teeth can be moved forward, backward, upward, downward and sideways. However, the surgical placement of these anchors in certain areas of the mouth is frequently very difficult because of limited access, thinness of the overlying soft tissue, irritations caused during routine oral functions, and the presence of nearby roots, nerves and blood vessels. Additionally. the means of attaching to these anchors is technically difficult and complicated mechanical objects are required to facilitate tooth movement and orthodontic corrections.

It is technically difficult to work in the back and roof of the mouth but the overlying tissue is thick. It is easy to work on the sides of the mouth opposite the upper teeth, but the overlying tissue is thin and irritation from the anchors and the presence of the roots of the teeth limit use in these areas. Right at the midline of the maxilla and mandible surgical access, tissue thickness and minimal irritation are present.

SUMMARY OF THE INVENTION

This invention can be adapted to any bony anchor system. Only a single anchor is needed and said anchor is placed in the front of the mouth and between the roots of the maxillary or mandibular central incisors. Onto a modified anchor head, an attachment is placed which stabilizes a rigid, heavy buccal wire. This wire in effect extends the influence of the anchor curvilinearly. Various attachments can be placed on this wire and from these attachments forces can be generated to move teeth.

This invention specifically addresses the shaped and design of the head of the bony anchor, the connector, the bony anchor extender and attachments placed on the bony anchor extender.

BRIEF DESCRIPTION OF THE DRAWINGS

These and other features and advantages of the present invention will become apparent from consideration of the following specifications when taken in conjunction with the accompanying drawings in which.

DETAILED DESCRIPTION OF THE EMBODIMENTS

Figure 1:
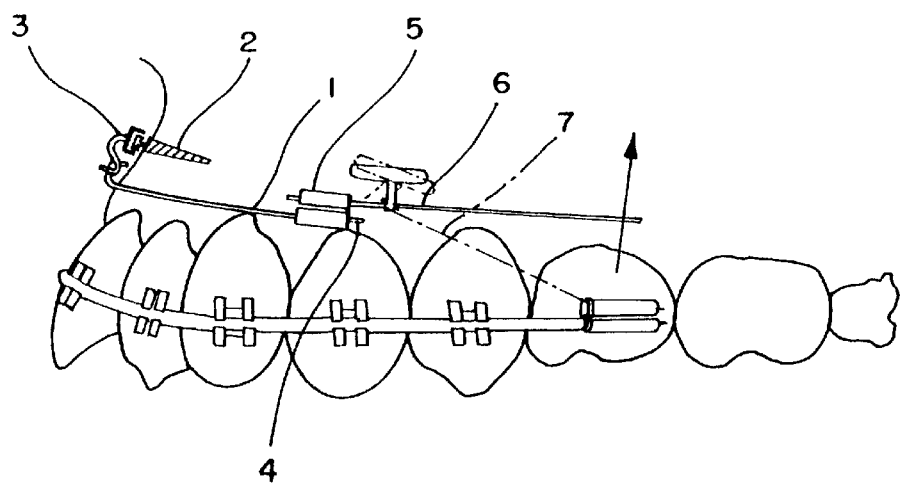
FIG. 1 is a side perspective view of the Bony Anchor Extender (BAE) showing the connector and a configuration for the head of the bony anchor while an intrusive force is being delivered to the posterior teeth from the BAE.

Referring now more particularly to FIG. 1., the Bony Anchor Extender (BAE) 1, is attached to a bony anchor 2 by a connector assembly 3. As the BAE extends distally it terminates as a free end 4. At any point along the BAE, attachments 5 can be placed and secured. From these attachments three dimensional movement of teeth or a tooth can be accomplished. In FIG. 1, an intrusive force is generated on the maxillary molar and to a lesser extent other posterior teeth by a wire shown in resting 6 and activated 7 (shown in dotted lines) states. Note that there is no equal and opposite effect on the anterior teeth.

Figure 2:
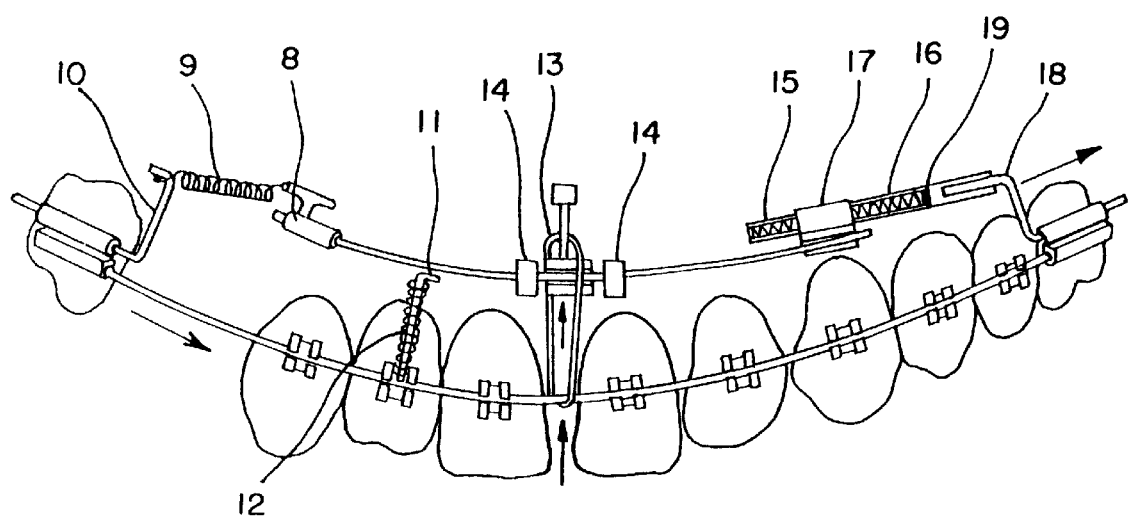
FIG. 2 is a front perspective of the present invention showing a distalizing force on the left molar while a mesializing force is being applied to the right molar because of missing teeth while an intrusion force is being applied to the central incisors.

In FIG. 2. the right molar is mesialized by attachment 8 at the distal of the BAE. A closed coil spring 9 hooks onto a vertically extending wire 10 which encourages translational movement to the first molar. A vertical attachment 11 and open coil spring 12 can selectively extrude one or more teeth while the elastic thread 13 intrudes the maxillary centrals. Stops 14 on the BAE and on each side of the connector stabilize the connector. The left molar is distalized by open coil spring 15 encased in a cylinder 16 which is attached to the BAE 17. A wire extension 18 attached to the molar is pressed upon by sliding plunger 19 of the distalizing cylinder/spring assembly 15, 16, 19.

Figure 3:
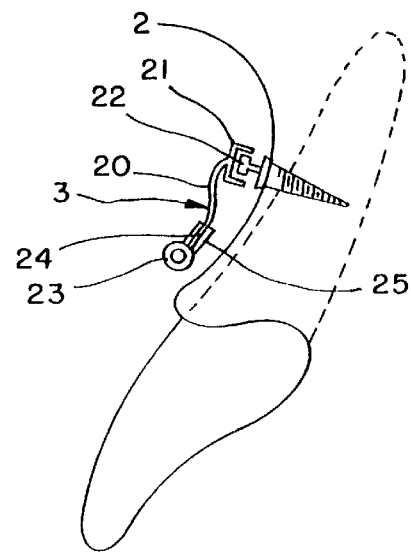
FIG. 3 is a schematic representation of the connector assembly.

FIG. 3 is an enlargement of FIG. 1 to better illustrate connector assembly 3 which consists of three components, wire midportion 20, the attachment 21 to the bony anchor head 22. and the attachment to the BAE 23. Note in this illustration that the midportion 20 fits into the attachment to the BAE 23 as illustrated at 24. The extended cylinder of the attachment 25, can be pressed firmly around the midportion 20 that fits into the BAE attachment 23. Then the entire BAE and attachment can be removed and either spot welded, soldered or stabilized in other ways so as to obtain a firm three dimensional configuration which can then be reinserted onto bony anchor head 22 and fixed by either a ligature wire or drop pin as illustrated in FIG. 6.

Figure 4:
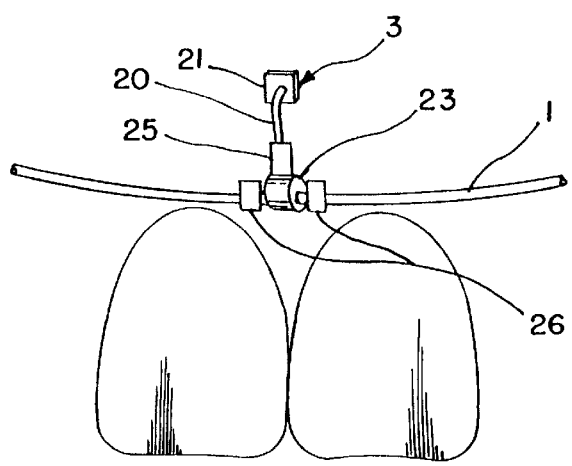
FIG. 4 is an enlarged front view of the connector assembly.

FIG. 4 is a frontal view of the connector assembly. The attachment to the bony anchor 21, the midportion 20 and the attachment to the BAE 23 are clearly visible. The way the connector fits into the vertical cylinder 25 of the BAE attachment 23 can be seen. Stops 26 on each side of BAE attachment 23 help stabilize the attachment assembly 3 onto BAE 1.

Figure 5A:
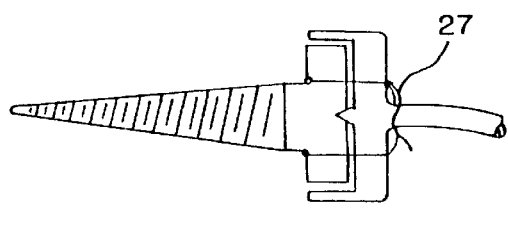
FIGS. 5a–5f illustrate the various configurations of the bony anchor head element.
Figure 5B:
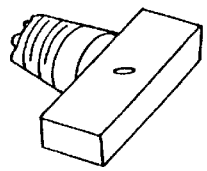
Figure 5C:
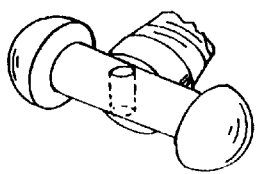
Figure 5D:
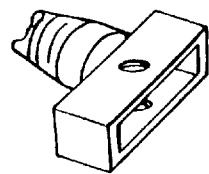
Figure 5E:
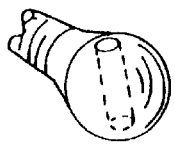
Figure 5F:
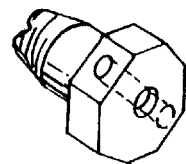

In FIGS. 5a–5f a variety of heads are illustrated which can either be placed on any bony anchor or be made an integral part thereof. More specifically, an angular head is shown in FIG. 5a, a solid wedge with flush ends is shown in FIG. 5b an enclosed wedge with rounded ends is shown in FIG. 5c, an open rectangular box is shown in FIG. 5d, a spherical head is shown in FIG. 5e, and an octagonal head is shown in FIG. 5f.

Figure 6A:
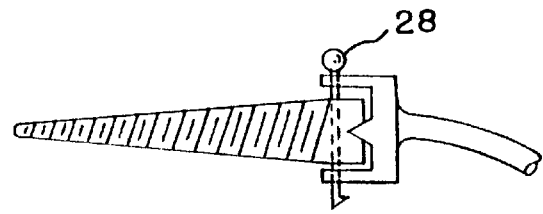
FIGS. 6a and 6b illustrate a means of attaching the connector to the head of the bony anchor.
Figure 6B:
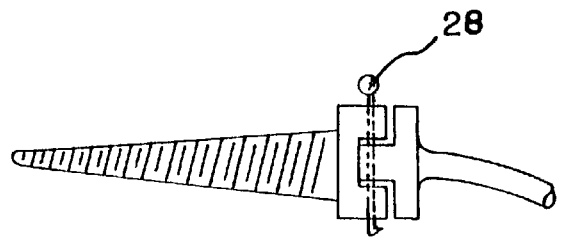

The connector assemblies are attachable to the bony anchor heads in FIGS. 5a–5e by ligature wire 27, as shown in FIG. 5a, or by drop pin 28, as shown in FIGS. 6a and 6b.

Figure 7:
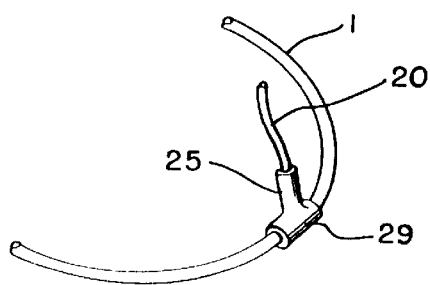
FIG. 7 shows a means of connection the midportion of the connector assembly to the BAE.

FIG. 7 illustrates a means of attaching the BAE to the bony anchor. A hollow T shaped crimpable cylinder 29 is placed onto BAE 1 and positioned by rotation and lateral movement to just that location where the midportion of the connector 20 can fit inside the vertical cylinder 25. Crimpable vertical cylinder 25 is then crimped along with the crimping of the other members of the T thereby securing the midportion in place. Thereafter BAE 1 and the connector assembly are removed from the mouth and these crimped portions of the hollow T shaped portion 29 are welded, soldered or secured in place by other means.

Figure 8:
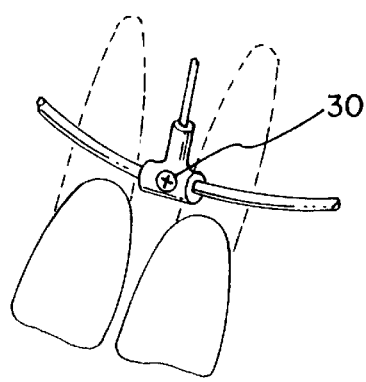
FIG. 8 depicts an adjustable screw clamp to attach the BAE to the connector assembly.
Figure 10A:
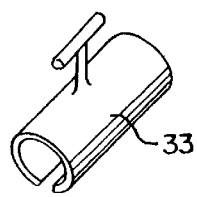
FIGS. 10a–10e show various attachments which can be placed on the BAE.

FIG. 8 is another means of making the connector attachment in which a screw clamp 30 is substituted for the crimpable aspects of hollow fitting 29 on the BAE.

Figure 9A:
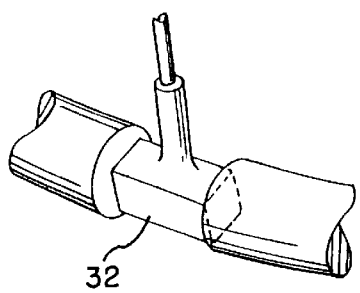
FIGS. 9a and 9b show a modification of the BAE at its midportion so as to fit an angular portion of the connector assembly.
Figure 9B:
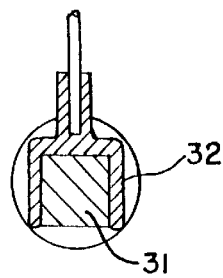

FIGS. 9a and 9b show another embodiment of the BAE in which center portion 31 is generally rectangular and cap 32 envelopes portion 31 at the BAE end of the attachment mechanism.

Figure 10C:
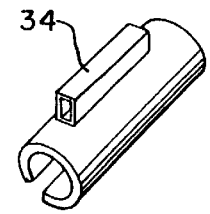
Figure 10B:
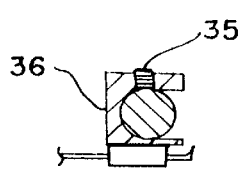
Figure 10E:
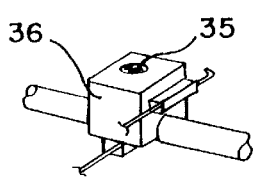
Figure 10D:
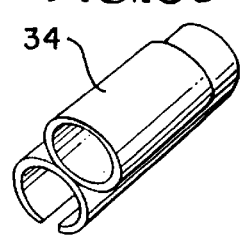

In FIGS. 10a–10e, a number of designs of the attachment which is placed on the BAE are depicted. Specifically shown is the crimpable nature of portion 33 which goes over the BAE and piggyback attachments 34 which are connected to the crimpable portion 33. FIGS. 10b and 10e show a piggyback tube or cylinder which is stabilized by means of locking screw 35 and clamp 36.

I claim:

1. An orthodontic appliance for moving teeth in a desired direction comprising a bony anchor for fixing in the oral cavity of a patient, an arch-shaped wire fixed to said bony anchor, a head formed on said bony anchor, a connector assembly comprising a first attachment means fixed to said head and a second attachment means fixed to said arch-shaped wire, and a midportion interconnecting said first and second attachment means.

2. An orthodontic appliance according to claim 1 wherein said head is generally rectangularly configured.

3. An orthodontic appliance according to claim 1 wherein said head is generally spherical in configuration.

4. An orthodontic appliance according to claim 1 wherein said head is generally square-shaped in configuration.

5. An orthodontic appliance according to claim 1 wherein said head is generally angular in configuration.

6. An orthodontic appliance according to claim 1 wherein said head is secured to said bony anchor by means of ligature wire.

7. An orthodontic appliance according to claim 1 wherein said head is secured to said bony anchor by means of a drop pin.

8. An orthodontic appliance according to claim 1 wherein said connector is attached to arch-shaped wire by means of a crimpable cylinder.

9. An orthodontic appliance according to claim 8 wherein a piggyback cylinder is secured to said crimpable cylinder.

10. An orthodontic appliance according to claim 9 wherein said piggyback cylinder is provided with a locking screw and clamp combination.

11. An orthodontic appliance according to claim 1 wherein said midportion comprises a wire.

* * * * *